United States Patent
Sebok et al.

(10) Patent No.: US 8,079,250 B2
(45) Date of Patent: Dec. 20, 2011

(54) VISCOMETER SYSTEM UTILIZING AN OPTICAL FLOW CELL

(75) Inventors: Thomas J. Sebok, Tallmadge, OH (US); Aaron M. Hagan, North Canton, OH (US); Joseph P. Kolp, North Canton, OH (US)

(73) Assignee: Lockheed Martin Corporation, Bethesda, MD (US)

( * ) Notice: Subject to any disclaimer, the term of this patent is extended or adjusted under 35 U.S.C. 154(b) by 691 days.

(21) Appl. No.: 12/169,923

(22) Filed: Jul. 9, 2008

(65) Prior Publication Data
US 2010/0005866 A1   Jan. 14, 2010

(51) Int. Cl.
*G01N 11/00*   (2006.01)
(52) U.S. Cl. .................... 73/54.43
(58) Field of Classification Search ........ 73/54.43; 356/335
See application file for complete search history.

(56) References Cited

U.S. PATENT DOCUMENTS

| | | | | |
|---|---|---|---|---|
| 3,198,064 A | 8/1965 | Moore | | 88/14 |
| 3,947,121 A | 3/1976 | Cotter et al. | | 356/38 |
| 4,393,466 A | 7/1983 | Deindoerfer et al. | | 364/415 |
| 4,804,267 A | 2/1989 | Greenfield | | 356/335 |
| 4,807,267 A | 2/1989 | Rifu et al. | | 378/7 |
| 5,030,421 A | 7/1991 | Muller | | 422/102 |
| 5,098,661 A | 3/1992 | Froehlich et al. | | 422/102 |
| 5,241,189 A | 8/1993 | Vandagriff et al. | | 250/575 |
| 5,594,544 A | 1/1997 | Horiuchi et al. | | 356/73 |
| 5,766,957 A | 6/1998 | Robinson et al. | | 436/165 |
| 5,883,721 A | 3/1999 | Gilby et al. | | 356/440 |
| 6,104,483 A | 8/2000 | Sebok et al. | | 356/244 |
| 6,290,912 B1 | 9/2001 | Doms | | 422/82.05 |
| 6,873,411 B2 | 3/2005 | Sebok et al. | | 356/335 |
| 2002/0092340 A1* | 7/2002 | Prater et al. | | 73/24.02 |
| 2005/0002030 A1* | 1/2005 | Kolp et al. | | 356/335 |
| 2005/0059926 A1* | 3/2005 | Sage et al. | | 604/65 |

FOREIGN PATENT DOCUMENTS

| | | |
|---|---|---|
| JP | 62-112034 | 5/1987 |
| JP | 7-218417 | 8/1995 |
| WO | WO 95/12118 | 5/1995 |

* cited by examiner

*Primary Examiner* — Hezron E Williams
*Assistant Examiner* — Tamiko Bellamy
(74) *Attorney, Agent, or Firm* — Renner Kenner Greive Bobak Taylor & Weber

(57) ABSTRACT

A viscometer system to determine the viscosity of a fluid utilizes an existing flow cell, which maintains a calibrated constriction that is defined by a predetermined constant value K is disclosed. The viscometer system is adapted for use with the flow cell and includes a pair of pressure transducers with one at the input of the flow cell and another at the outlet of the flow cell. During operation, particles within the fluid pass through the flow cell, whereby the positional change of the particles over a predetermined period of time allows the system to calculate the flow rate of the fluid. The system also identifies the change in pressure of the fluid as it passes through the flow cell, such that the pressure change, flow rate, and the constant value K are processed to calculate the viscosity of the fluid being analyzed.

24 Claims, 10 Drawing Sheets

VISCOMETER SYSTEM UTILIZING AN OPTICAL FLOW CELL

TECHNICAL FIELD

Generally, the present invention relates to a system for deriving the viscosity of a fluid using an optical flow cell maintaining a calibrated constriction. Particularly, the present invention relates to a system for deriving the viscosity of a fluid based on the movement of detected particles carried by the fluid through a flow cell. More particularly, the present invention relates to deriving the viscosity of a fluid at a selected temperature based on the change in pressure of the fluid passing through an optical flow cell, the calibrated constriction constant of the flow cell, and the flow rate of the fluid.

BACKGROUND ART

In the past, the viscosity of a fluid has been measured utilizing a number of systems and techniques. For example, viscosity may be identified by measuring the force required to move a piston through a fluid, measuring the decay rate associated with a tuning fork excited within a fluid, measuring the time it takes a metal ball to roll down an incline within a fluid sample, or by measuring the time it takes a sample volume of fluid to exit through a constriction as it is pulled by gravitational forces.

However, many manners of determining viscosity generally require that the fluid sample be removed from the machine or other device that maintains the fluid for subsequent analysis. For example, oil used in an engine needs to be extracted and then separately analyzed on a testing bench to ascertain its viscosity. Such an endeavor generally requires that the machine be taken off-line or otherwise placed in an inoperable state so that the appropriate personnel can access the vehicle to extract the oil for testing. Unfortunately, the inoperability of the machine, results in a loss of productivity for those reliant on its operation. Thus, such techniques for assessing fluid viscosity are generally inefficient, and impose added operating costs, as the equipment utilizing the fluid to be analyzed must be taken out of service before testing of the fluid can be performed.

In addition, while many existing viscometers are capable of determining the viscosity of a fluid over various ranges of flow rates, most of these devices are not capable of accurately determining viscosity when fluid flow rates are low. As such, the operator or supervisor overseeing the operation of a machine or other equipment that utilizes low fluid flow rates is required to rely primarily on the performance specifications defined by the manufacturer of the fluid, which is generally undesirable when maintaining the operation of costly equipment that cannot readily be replaced.

There has recently been a trend toward utilizing debris analysis monitors, such as optical flow cell monitors, to analyze and detect debris that may be present in the lubricating fluid used by a machine. Such debris monitors facilitate the determination of a wear condition of the machine, and allow maintenance technicians to accurately identify when the fluid needs replacement and/or whether a particular operating component of the machine is in need of repair. However, such debris analysis monitors provide only data relating to the wear state of the machine, which maintains the fluid, and does not provide any information concerning the viscosity of the fluid. As such, operators of machines that employ the use of a flow cell are currently required to install another separate system in order to identify the viscosity of the fluid. Unfortunately, such viscosity measurement systems are costly, and tend to be bulky, making them potentially difficult to be installed in and about various machines.

The determination of a fluid's viscosity is beneficial in assessing whether the components of the fluid have been broken down or have degraded beyond a safe point. Furthermore, the determination of viscosity is beneficial in identifying the performance parameters or characterizing other parameters of the fluid so that the operation of a machine that utilizes the fluid can be monitored for potential adverse events.

Therefore, there is a need in the art for a viscometer system to derive fluid viscosity utilizing a flow cell with a calibrated constriction and a pressure sensor. Furthermore, there is a need for a viscometer system that can be retrofit, or otherwise added-on to the components of an existing flow cell to derive fluid viscosity. And, there is a need in the art for a viscometer system to derive fluid viscosity that is compact in size allowing the system to be incorporated with a machine whose fluid is being monitored. There is also a need in the art for a viscometer system to derive fluid viscosity over a wide viscosity and temperature range. Still yet there is a need for a viscometer system that can accurately derive the viscosity of a fluid having low flow rates.

SUMMARY OF INVENTION

In light of the foregoing, it is a first aspect of the present invention to provide a viscometer system utilizing an optical flow cell.

It is another aspect of the present invention to provide a system for determining the viscosity of a fluid, the system comprising a flow cell having an inlet and an outlet, and a calibrated constriction defined by a constant value K, the flow cell providing an imaging system to identify particles flowing therethrough, a first pressure transducer fluidly coupled to the inlet of the flow cell inlet, the inlet pressure transducer receiving a flow of fluid, a second pressure transducer fluidly coupled to the flow outlet, and a controller adapted to be coupled to the first and second pressure transducers, and to the imaging system, wherein the controller is configured to control the imaging system to identify the movement of a particle carried by the fluid so as to calculate a flow rate of the fluid, and wherein the controller determines the viscosity of the fluid based on the constant value K associated with the flow cell, the flow rate and the change in pressure in the fluid at the first and second pressure transducers.

Yet another aspect of the present invention is to provide a method for determining a viscosity of a fluid flowing through a flow cell comprising providing a flow cell with a constriction having a flow resistance defined by a predetermined constant value, the flow cell having an inlet and an outlet, the flow cell configured to receive a flow of fluid therethrough and to detect the movement of at least one particle, coupling a first pressure transducer at the inlet and a second pressure transducer at the outlet, determining a flow rate of the fluid through the flow cell based on a change in position of at least one detected particle, determining a change in pressure of the fluid between the inlet and the outlet of the flow cell, and calculating a viscosity of the fluid based on the flow rate, the change in fluid pressure, and the predetermined constant value.

Still another aspect of the present invention is a manifold for determining a pressure of a flow of fluid via a pressure sensing element, the manifold comprising a body maintaining an inlet port and an outlet port that each extend into a flow basin, wherein the inlet port and the outlet port are laterally offset from each other, and a seal disposed about the perimeter of the flow basin, wherein the pressure sensing element is disposed thereon, such that fluid flows between the inlet port and the outlet port and in contact with the pressure sensing element.

Yet another aspect of the present invention is a method of determining the viscosity of a fluid flowing through a flow cell at a desired temperature comprising providing a flow cell maintaining a constriction, the flow through which is defined by a constant value K, and an imaging system configured to generate a light pulse to image particles carried by the fluid passing through the flow cell, providing a pressure transducer to monitor a change in pressure of the fluid flowing through the flow cell, determining a distance moved by each imaged particle during a predetermined period of time, and identifying a flow rate of the fluid based on the average of the distance values and the predetermined period of time, and determining a viscosity of the fluid based on the constant value K, the flow rate of the fluid, and the change in pressure of the fluid as it passes through the flow cell at the desired temperature.

BRIEF DESCRIPTION OF THE DRAWINGS

These and other features and advantages of the present invention will become better understood with regard to the following description, appended claims, and accompanying drawings wherein:

BEST MODE FOR CARRYING OUT THE INVENTION

Figure 1:
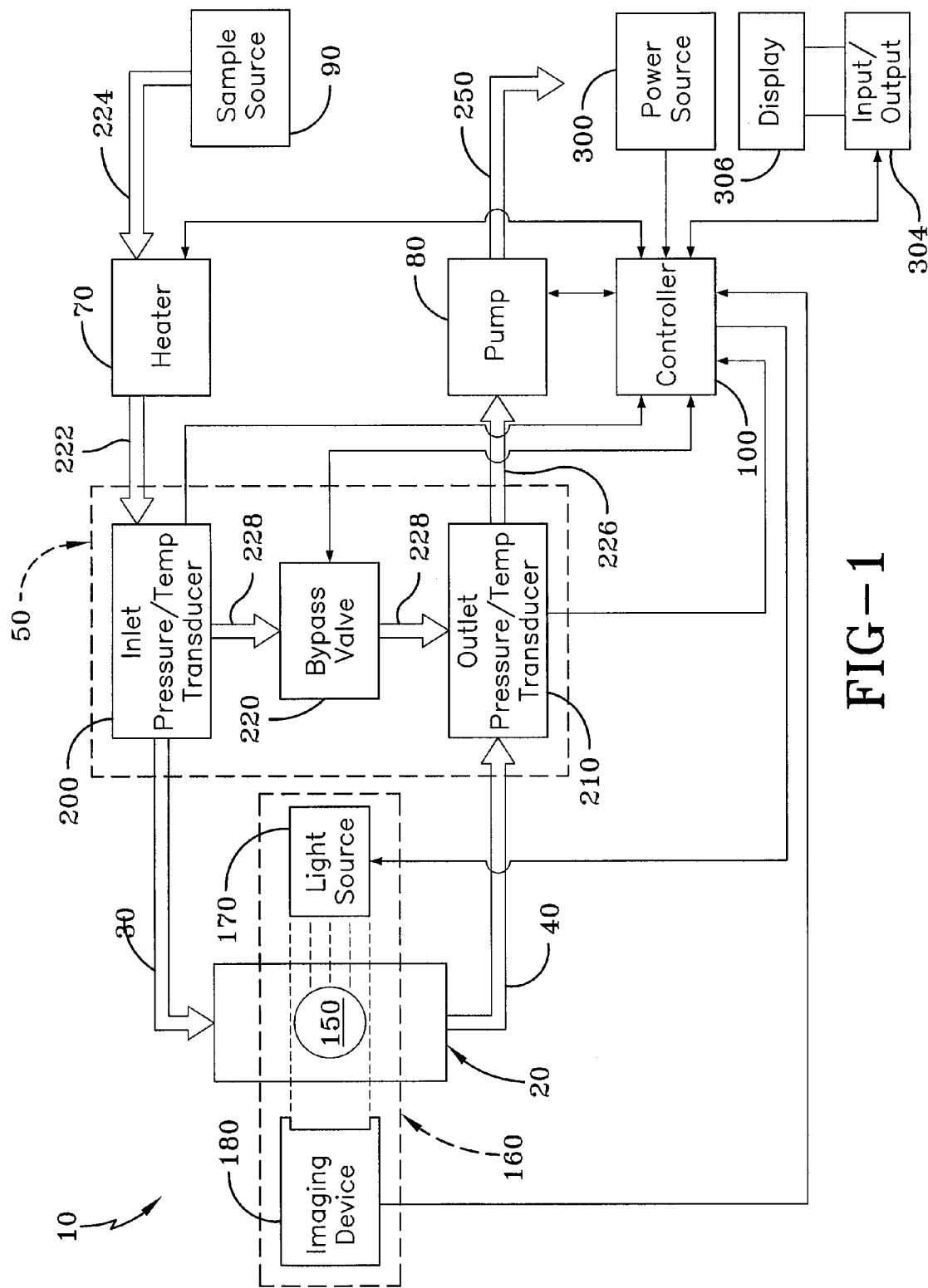
FIG. 1 is a schematic diagram of a viscometer system that is configured to use the operation of an installed flow cell to determine the viscosity of a fluid passing therethrough in accordance with the concepts of the present invention.

A viscometer system utilizing a flow cell for determining the viscosity of a fluid is generally referred to by the numeral 10, as shown in FIG. 1 of the drawings. For the purposes of the following discussion, the term "fluid" is defined to include any fluid or liquid suitable for use with the viscometer 10.

Continuing, the viscometer system 10 is configured for use with an installed optical flow cell 20 that is used for analyzing, or otherwise detecting particles or debris carried by a fluid flowing therethrough. An inlet tube 30 is coupled at one end of the flow cell 20, while an outlet tube 40 is coupled to the other end of the flow cell 20 to allow for the flow of fluid therethrough. As such, the end of the flow cell 20 to which the inlet tube 30 is coupled serves as the inlet to the flow cell 20, while the end of flow cell 20 to which the outlet tube 40 is coupled serves as the outlet to the flow cell 20. Furthermore, the flow cell 20 maintains a calibrated passage or constriction between its inlet and outlet whose resistance to the flow of fluid therethrough is defined, or otherwise quantified by a constant value K. While the viscometer 10 is capable of determining the viscosity of a fluid having a wide range of flow rates, the viscometer 10, through the use of the optical flow cell 20, is particularly suited to derive the viscosity of fluids having a low flow rate, such as about 2 mL/min. for example, however such should not be construed as limiting as any other suitable flow rate may be used.

A pressure/temperature transducer assembly 50 is fluidly coupled between the inlet tube 30 and the outlet tube 40 of the flow cell 20. The assembly 50 is enabled to monitor the change in pressure of the fluid as it passes through the flow cell 20, as well as to predict or otherwise identify the temperature of the fluid within the calibrated constriction maintained the flow cell 20. The system 10 also includes a heater 70 to heat the fluid supplied to the inlet tube 30 to a desired temperature, while a pump 80 is configured to draw fluid from a fluid source 90, such as a reservoir, through the heater 70, the assembly 50, the flow cell 20 and components of the system 10.

To determine the viscosity of the fluid, the system 10 determines the flow rate of the fluid and its change in pressure as it passes through the flow cell 20. In addition to the calculation of viscosity, the system 10 is also configured to associate identified viscosity values with particular temperature values, which will be discussed in more detail below. Generally, viscosity values at selected temperatures, i.e. 40° C. or 100° C., are calculated by extrapolating from the measured viscosity at the measured temperature. This data is collected and processed by a suitable controller 100, where it is processed along with the constriction constant K defining the flow resistance associated with the particular flow cell 20 being used to determine the viscosity of the fluid at a given temperature. As such, the viscometer system 10 may be added-on, or otherwise retrofit with an existing flow cell 20 and controller 100 to enable the determination of the viscosity of a fluid. However, the viscometer system 10 may take on other configurations, whereby the controller 100 may be provided together with the viscometer 10, such that the controller 100 is pre-programmed to enable the operation of the viscometer 10. For example, in the case where the viscometer is configured as an on-line system, the analysis to determine fluid viscosity may be performed by a processor embedded or otherwise maintained by an imaging device discussed below.

The viscometer system 10 comprises the flow cell 20, such as that described in U.S. Pat. No. 7,184,141, which is incorporated herein by reference. The system 10 includes an imaging/light receiving aperture 150 that enables various particles within a flow of fluid to be imaged by an imaging system 160, such as that described in U.S. Pat. No. 7,019,834, which is incorporated herein by reference. The imaging system 160 includes a light source 170, such as a laser, that generates a light beam received by the imaging/light receiving aperture 150, so as to illuminate one or more particles within the fluid flowing through the flow cell 20. The illuminated particles are then detected by an imaging device 180, such as a camera, that is positioned opposite the light source 170. In one aspect, the imaging device 180 may be carried or mounted upon a suitable bracket, such as that described in U.S. Pat. No. 7,019,834, which is incorporated herein by reference.

Coupled to the inlet tube 30 and the outlet tube 40 of the flow cell 20 is the pressure/temperature transducer assembly 50. The transducer assembly 50 comprises an inlet pressure/temperature transducer 200 and an outlet pressure/temperature transducer 210 that are fluidly coupled by a bypass valve 220. It should be appreciated that either of the pressure or temperature transducers maintained by either of the inlet or outlet pressure/temperature transducers 200,210 may be comprised of other types of pressure and/or temperature sensors. In particular, the pressure/temperature transducer assembly 50 is configured such that the inlet tube 30 is coupled between the inlet of the flow cell 20 and the inlet pressure/temperature transducer 200, while the outlet tube 40 is coupled between the outlet of the flow cell 20 and the outlet pressure/temperature transducer 210. The viscometer system 10 also includes the heater 70 that is fluidly coupled at one end to the inlet pressure/temperature transducer 200 via an intermediate tube 222, while the other end of the heater 70 is coupled to an intake tube 224 that is configured to receive a suitable fluid sample for analysis from the sample source 90. The heater 70 is configured to heat the fluid drawn from the sample source 90 as it flows through the inlet tube 30 and into the flow cell 20. To generate a flow of fluid through the system 10, such as in an off-line viscometer, the pump 80 is fluidly coupled at one end to the outlet pressure/temperature transducer 210 via an intermediate tube 226 and at another end to an exit tube 250, where the analyzed fluid leaves the system 10. However, it should be appreciated that the pump 80 is optional and not required for the operation of the viscometer 10, as a fluid flow through the system 10 may be generated by providing any suitable pressure differential between the inlet tube 30 and outlet tube 40 coupled to the flow cell 20 using any suitable means. For example, should the system 10 be utilized in an on-line or in-line configuration, the inlet and outlet tubes 30,40 are coupled or "tapped into" an existing fluid source so as to provide a suitable pressure differential between the inlet and outlet tubes 30, 40 to generate a flow of fluid through the flow cell 20. Thus, suitable fluid flow through the flow cell 20 is achieved when the viscometer 10 is used in various configurations, such as in an on-line, in-line, and off-line configurations.

Furthermore, the bypass valve 220 is coupled between the pressure/temperature transducers 200, 210 via a bypass tube 228. As such, the viscometer system 10 is configured to maintain two fluid paths that are controlled based on the state (open/closed) of the bypass valve 220. Thus, when the bypass valve 220 is closed, fluid is prevented from passing through the bypass valve 220, and is routed or drawn through the intake tube 224, the heater 70, the inlet pressure/temperature transducer 200, the flow cell 20, the outlet pressure/temperature transducer 210, and the pump 80, whereupon the fluid is evacuated from the system 10 at the exit tube 250. And when the bypass valve 220 is open, fluid bypasses the flow cell 20, and passes through the bypass valve 220, whereupon the fluid is routed or drawn through the intake tube 224, the heater 70, the inlet pressure/temperature transducer 200, the outlet pressure/temperature transducer 210, and the pump 80, whereupon the fluid is evacuated from the system 10 at the exit tube 250. In one aspect, the exit tube 250 may be configured to evacuate the fluid back into the sample source 90.

Due to the design of the flow cell 20, the passage or constriction through the flow cell 20 that fluidly connects the inlet tube 30 with the outlet tube 40 is calibrated such that the resistance to the flow of fluid through the flow cell 20 is defined by a constant value K, which will be discussed in further detail below. Generally though, when the viscometer system 10 is put into use, the constriction value K that defines the resistance to flow through the flow cell 20 is determined. Once identified, the value K can be loaded and stored at the controller 100 so that it may be utilized in a manner to be discussed. Alternatively, the controller 100 may be pre-programmed with the appropriate constriction constant K that corresponds to the flow resistance imparted by the flow cell 20 being used.

To coordinate the operation of the system 10, the controller 100 is coupled to the light source 170, the imaging device 180, the inlet and outlet pressure/temperature transducers 200, 210, the bypass valve 220, the heater 70, and the pump 80. As appropriate, each component connected to the controller 100 may provide operational status information to thereto so that operation of other connected components may be modified. In addition, the controller 100 may comprise any general purpose or application-specific computing device that is suitable for carrying out the operation of the system 10. To store various data, including the constriction constant value K, the controller 100 may include volatile memory, non-volatile memory, or a combination of both.

A power source 300, which may comprise a portable power source, such as a battery, or a wired power source, such as mains power provided by a wall outlet, is used to power the controller 100, and may be used to power the other components of the system 10 as well. Furthermore, the controller 100 may be preprogrammed and configured with the necessary communication interface to permit the components of the pressure/temperature transducers 200,210, heater 70, and pump 80 to be coupled thereto. Moreover, such a configuration is beneficial when the viscometer system 10 is configured as a system that is later added or retrofitted with a previously installed flow cell 20. In addition, the controller 100 may also be programmed in advance to accommodate the control and processing functions that are necessary for the system 10 to acquire the necessary data from the flow cell 20 and the temperature/pressure transducers 200,210. And to process the data using the appropriate algorithms in which to derive the viscosity of the fluid, as will be discussed below. An input/output device 304 may be connected to the controller 100 so that a user may provide instructions for operation of the system. A user-readable display is connected to the input/output device 304. The device 304 and display 306 may be separately powered.

Figure 2:
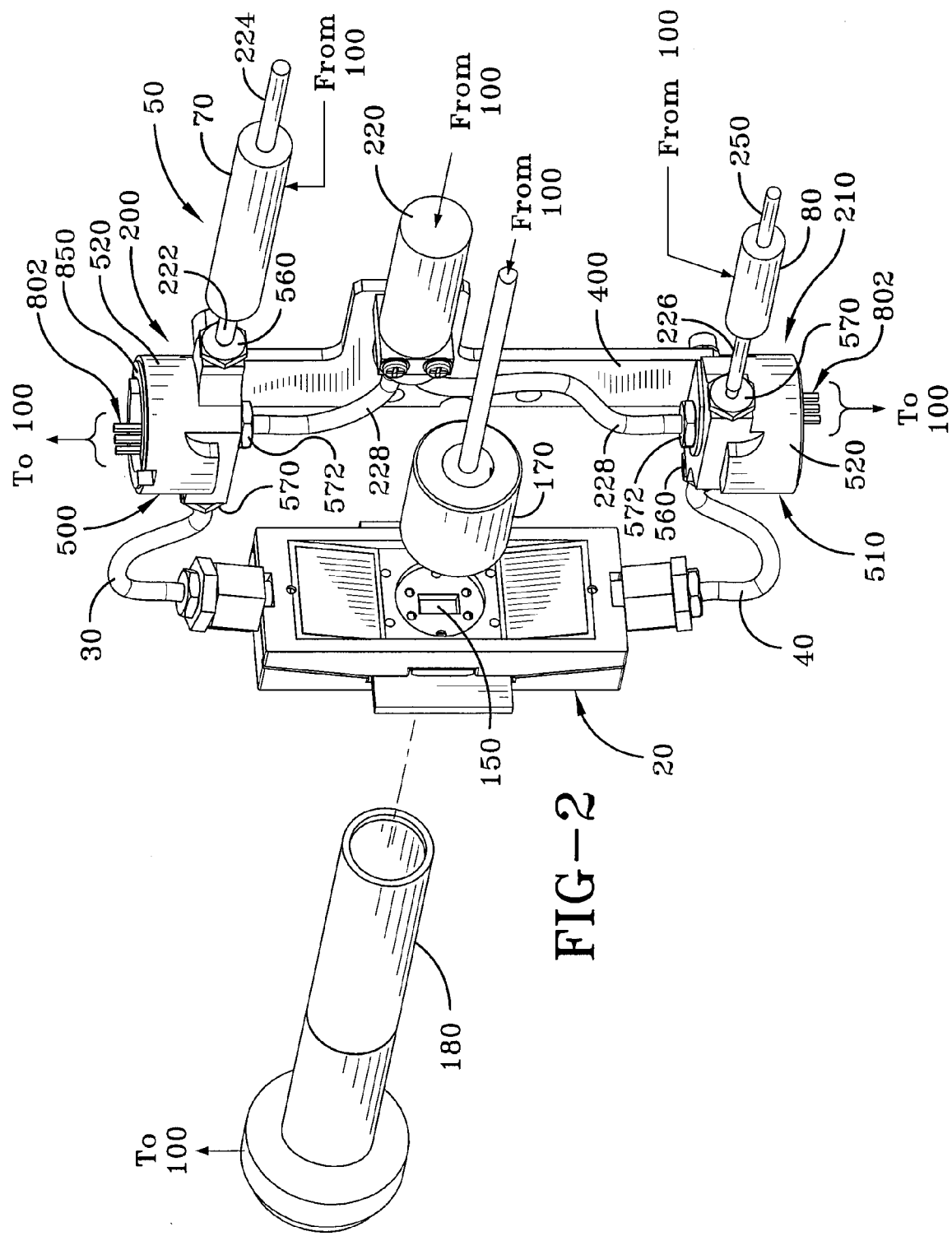
FIG. 2 is a perspective view of the viscometer system, in which pressure/temperature transducers are maintained in respective manifolds with minimal thermal mass in accordance with the concepts of the present invention.
Figure 3:
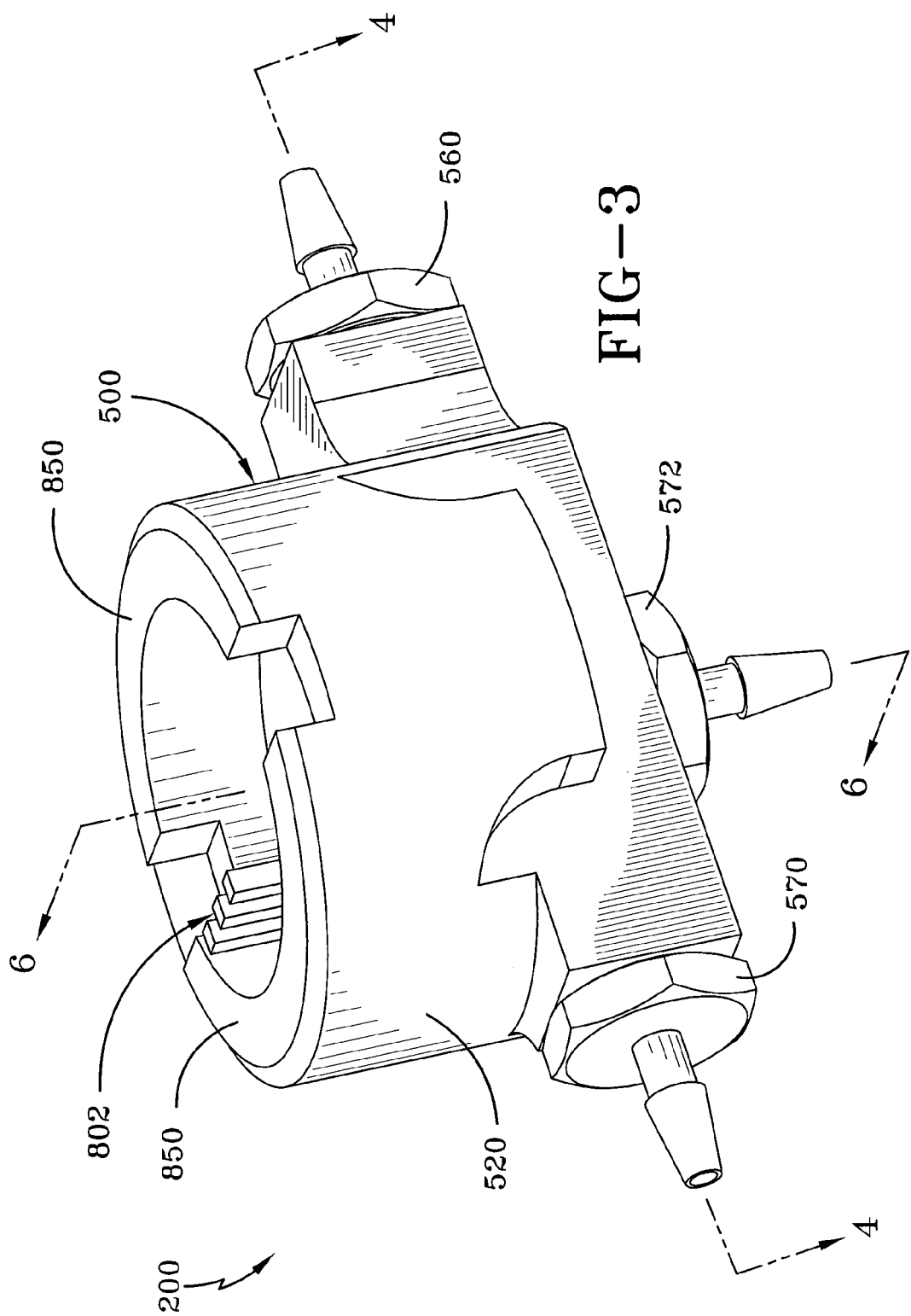
FIG. 3 is a perspective view of one of the manifolds used by the viscometer system in accordance with the concepts of the present invention.

Continuing to FIG. 2, the system 10 is shown, whereby the inlet and outlet pressure/temperature transducers 200,210 and the bypass valve 220 are carried by a mounting bracket 400. The mounting bracket 400 may comprise any suitable material, including but not limited to steel, aluminum, and plastic that is suitable for supporting the inlet and outlet pressure/temperature transducers 200,210 and the bypass valve 220.

In one aspect, the inlet and outlet pressure/temperature transducers 200,210 may be maintained within respective manifolds 500 and 510, as shown in FIG. 2, and in more detail in FIGS. 3-7. Because the manifolds 500 and 510 are structurally and operationally equivalent, only a discussion of the components of the manifold 500 will be presented below. The manifold 500 comprises a body 520 that is formed from aluminum, such as 6061-T1 aluminum, stainless steel, or any other suitable material, including but not limited to polymeric material, and is configured so that the thermal mass of the manifold 500 is minimal. That is, due to the design of the manifold 500 it is able to quickly take on or match the temperature of fluid passing therethrough. Such ability is highly desirable, as it allows the system 10 to efficiently adapt to temperature changes in the fluid induced by the heater 70. Thus, should the user desire to test fluid viscosities at varying temperatures, a large volume of fluid is not required to be passed through the manifold 500 in order for the manifold 500 to match the desired temperature of the fluid. Such operation reduces setup time and therefore increases the efficiency in which the system 10 operates.

Figure 4:
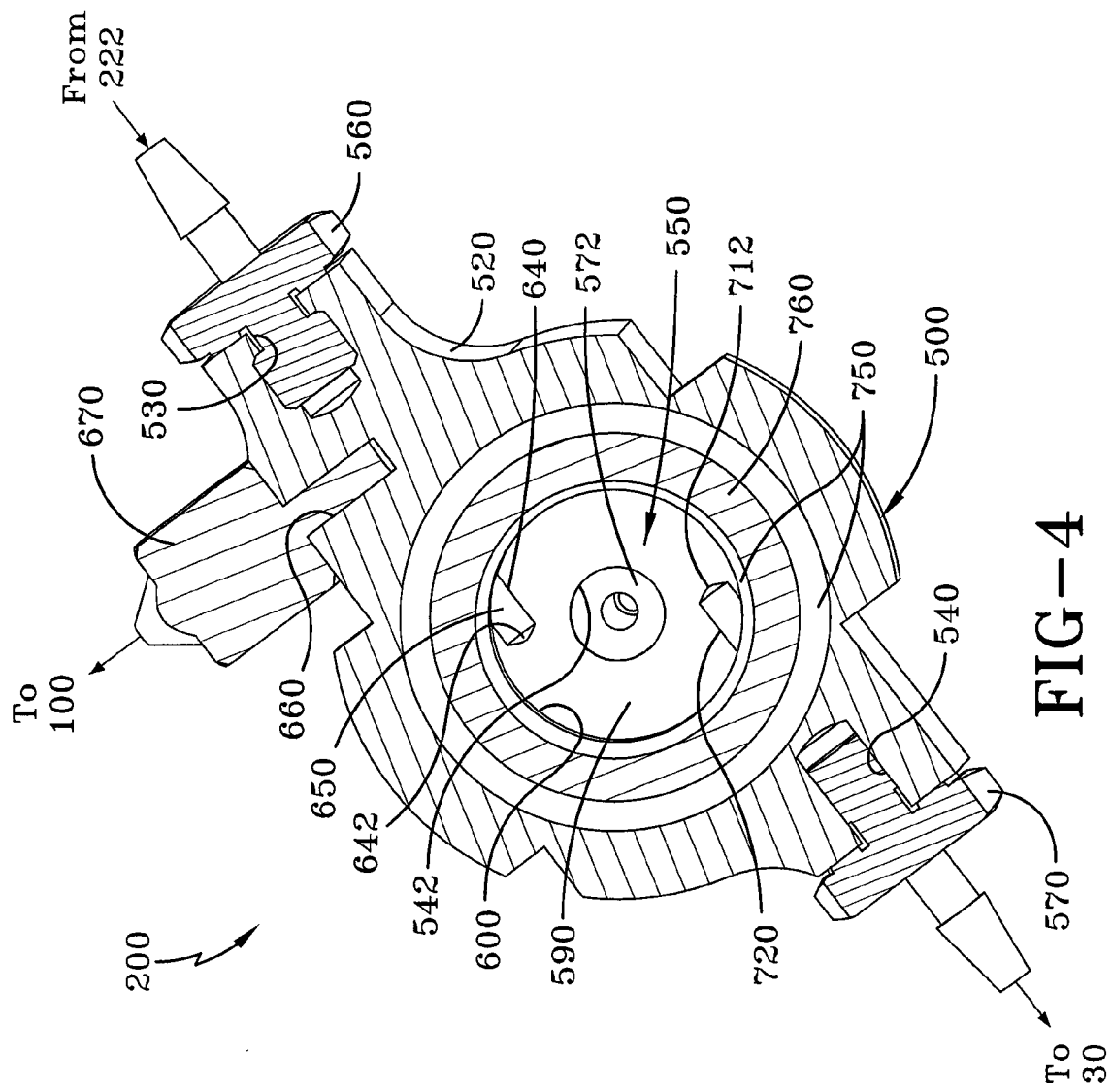
FIG. 4 is a perspective cross-sectional view of the manifold taken along lines 4-4 of FIG. 3 showing a flow basin maintained by the manifold in accordance with the concepts of the present invention.
Figure 5:
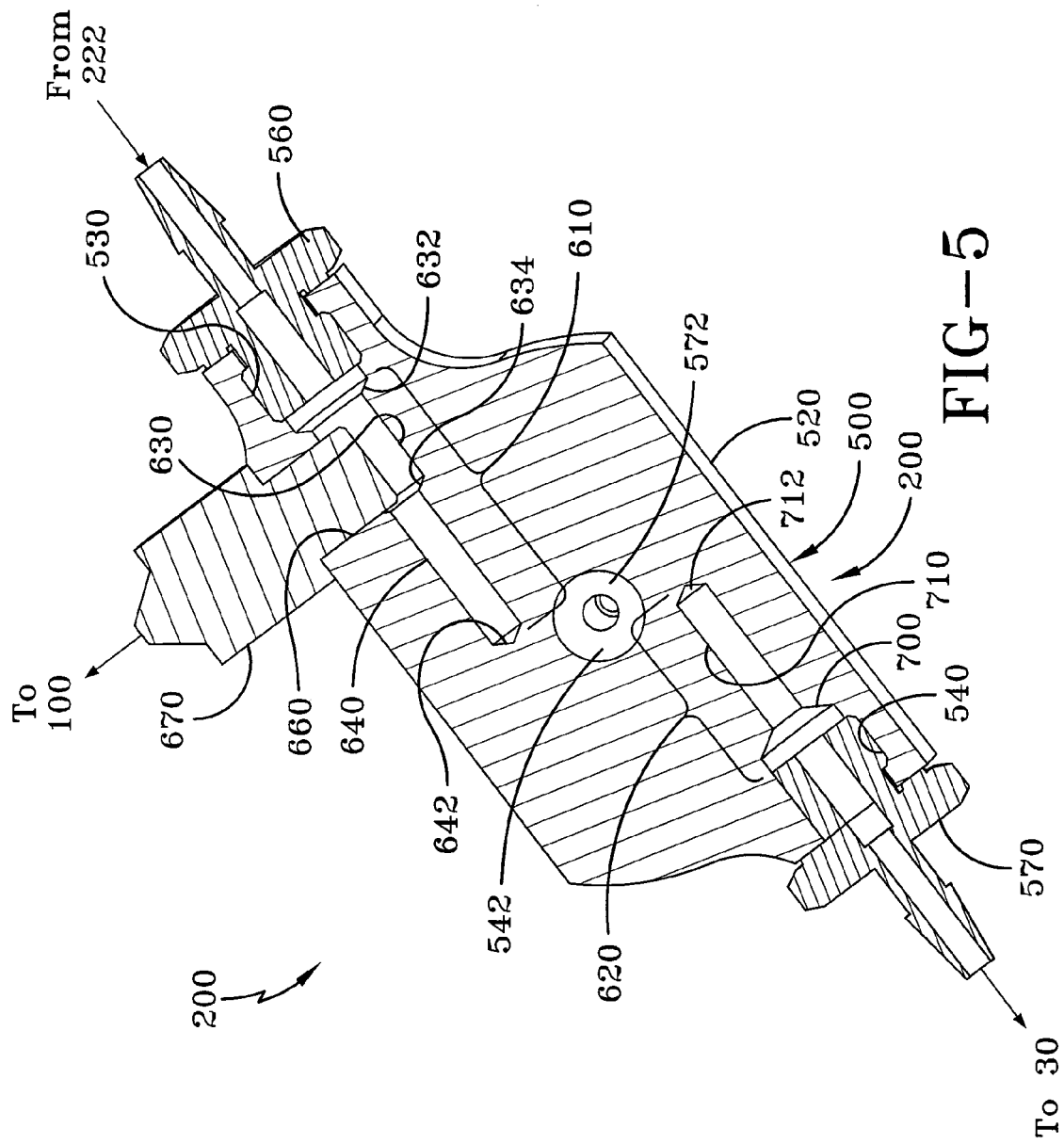
FIG. 5 is a perspective cross-sectional view of the manifold showing the components of the inlet port and the outlet port in accordance with the concepts of the present invention.
Figure 6:
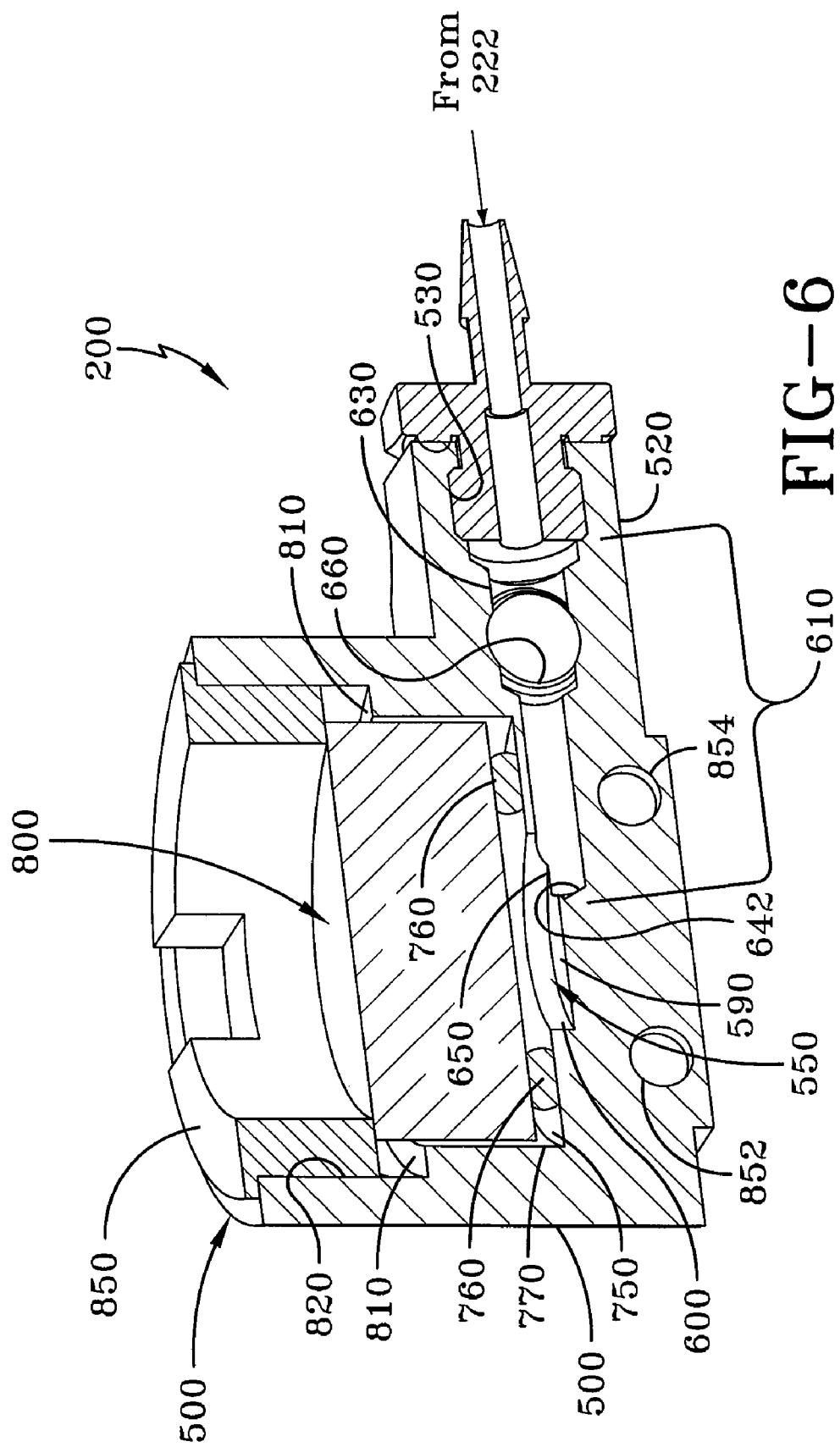
FIG. 6 is a perspective cross-sectional view of the manifold taken along lines 6-6 of FIG. 3 showing an attachment bore maintaining a temperature sensing element in accordance with the concepts of the present invention.
Figure 7:
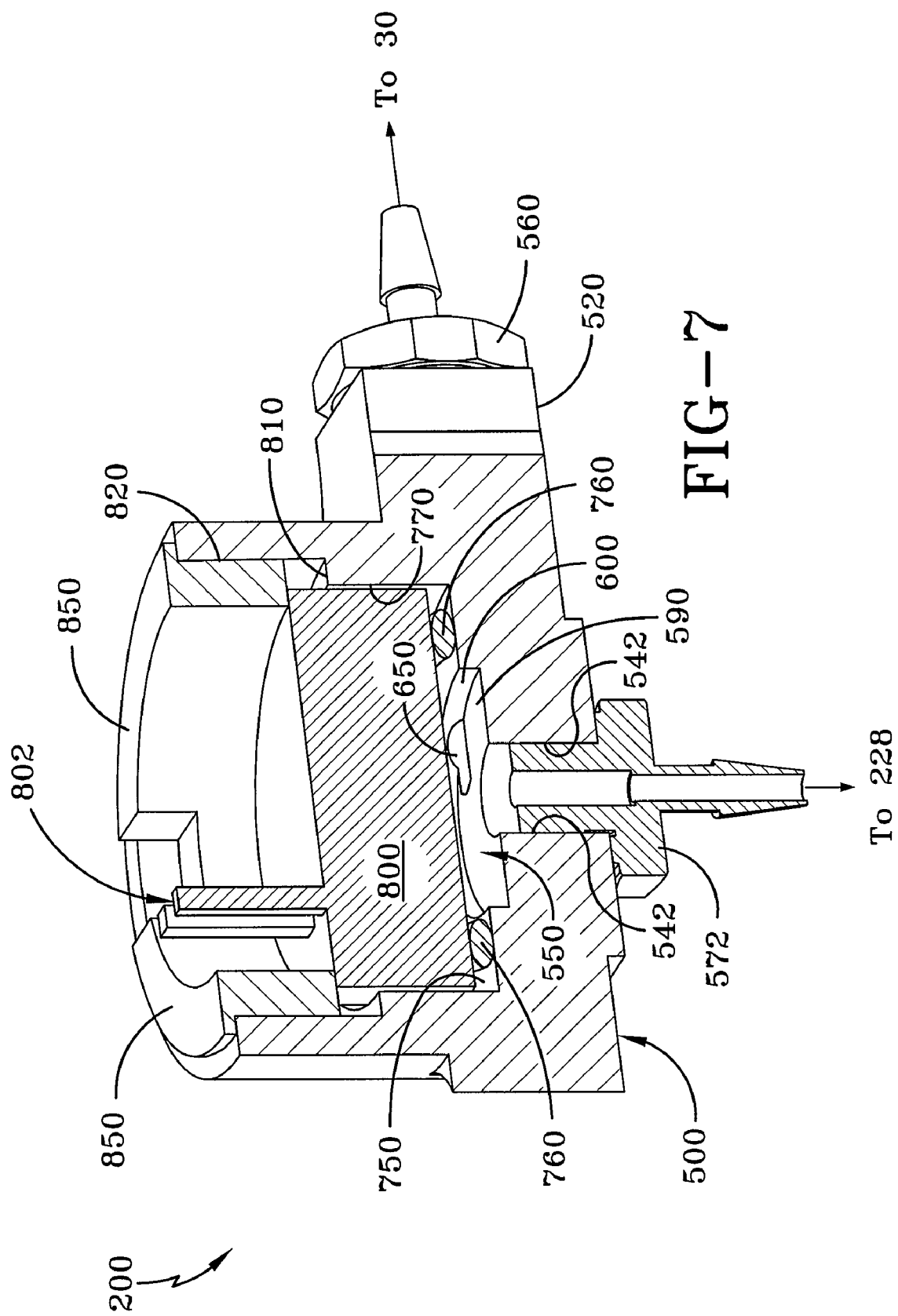
FIG. 7 is a perspective cross-sectional view of the manifold showing a bypass port according to the concepts of the present invention.

Continuing, with reference to FIGS. 3-7, the manifold body 520 of the manifold 500 maintains a manifold inlet port 530, a manifold outlet port 540, and a manifold bypass port 542, which are fluidly coupled by a flow basin 550, shown more clearly in FIG. 4. The inlet, outlet, and bypass port 530,540,542 are configured to receive corresponding connectors, such as threaded connectors 560,570,572 which are configured to provide a suitable connection with the intermediate tube 222, the inlet tube 30 and the bypass tube 228, respectively. However, in the case of the manifold 510 the threaded connectors 560,570,572 are configured to provide a suitable connection with the outlet tube 40, the intermediate tube 226, and the bypass tube 228 respectively. In particular, as shown in FIGS. 4-7, the flow basin 550 comprises a substantially annular base surface 590 that is bounded or circumscribed by a cylindrical wall 600. The inlet port 530 and the outlet port 540 extend into the flow basin 550 via respective inlet and outlet passages 610,620, as shown clearly in FIG. 5. The inlet passage 610, which extends from the inlet port 530 comprises an outer bore 630 that extends between an outer nozzle surface 632 to an intermediate nozzle surface 634. Additionally, the inlet passage 610 also includes an inner bore 640 that extends from the intermediate nozzle surface 634 to a tapered end surface 642 that extends beyond the wall 600, so as to form a basin inlet opening 650, shown in FIG. 4, that is disposed within the wall 600 and the base surface 590 flow basin 550. Fluidly coupled to the outer bore 630 is an attachment bore 660, such as a threaded bore, that is configured to receive and maintain a temperature sensing element 670, such as a thermocouple which is connected to the controller 100.

The manifold outlet port 540 extends into the flow basin 550 via the outlet passage 620, which comprises an outer nozzle surface 700 from which extends an inner bore 710. The inner bore 710 extends beyond the wall 600 and terminates at a tapered end surface 712, so as to form a basin outlet opening 720, shown in FIG. 4, that is disposed within the wall 600 and the base surface 590 of the flow basin 550. The basin inlet and outlet openings 650,720 are oriented such that they are laterally offset from each other and laterally offset with the bypass port 542.

Separated from the base surface 590 by the wall 600 is an upper basin surface 750 that is concentric with the base surface 590. The upper basin surface 750 is substantially annular and is configured to support and retain a seal 760, such as an o-ring for example, disposed thereon. A substantially cylindrical intermediate wall 770 bounds the outer periphery of the upper basin surface 750 and is dimensioned such that a pressure sensing element 800, such as a MEMS (micro-electro-mechanical sensor) pressure sensing device, may be disposed therein. In one aspect, it should be appreciated that the sensing element 800 provides suitable connection terminals 802 to facilitate attachment to the controller 100. In particular, the pressure sensing element 800 is dimensioned to rest upon the seal 760, such that the flow of fluid through the manifold 500 is contained by the base surface 590, the wall 600 of the flow basin 550, and the pressure sensing element 800. An annular intermediate surface 810, which is concentric with the base surface and the upper basin surface 750, is disposed about the perimeter of the intermediate wall 770, from which extends an outer cylindrical wall 820. Disposed upon the intermediate surface 810 and against the outer wall 820 is a retainer ring 850 used to retain the pressure sensing element 800 within the manifold 500 so that it is in operative relation with fluid as it moves through the flow basin 550. It should be appreciated that the retainer ring 850 and the wall 820 may include suitable threads for allowing the retaining ring 850 to be threadably fastened to the manifold. It should also be appreciated that the manifold 500 may include bores 852,854 for mounting the manifold 500 to a bracket, such as the bracket 400, via suitable fasteners.

In operation, when the flow of fluid through the bypass port 542 is prevented by closing the bypass valve 220, fluid enters the inlet port 530 via the threaded connector 560. Upon entering the inlet port 530, the fluid moves through the inlet passage 610, where it passes through the outer bore 630 and the inner bore 640 and enters the flow basin 550 via the basin inlet opening 650. As the fluid flows through the flow basin 550, it exits the flow basin 550 via the basin outlet opening 720, whereupon the fluid leaves the manifold 500 via the outlet passage 620 and threaded connector 570. Due to the dimensions of the flow basin 550 and the laterally offset positioning of the basin inlet and basin outlet openings 650,720, a circular flow of fluid is formed within the flow basin 550. As such, the flow basin 550 provides a volume or region that is fully pressurized by the fluid at all times. The flow basin 550 was designed to minimize the formation of dead zone regions (i.e. regions of low or no pressure) where the fluid and/or particles may stagnate, or otherwise collect are prevented. Thus, the manifold 500 does not "filter" the fluid of any particles that are carried by the fluid as it passes through the flow basin 550, but rather enables the fluid and particles carried thereby to freely pass therethrough without accumulating within the flow basin 550. Such operation is beneficial, as the detection of particles by the flow cell 20 facilitates the ability of the system 10 to calculate the viscosity of the fluid that is carrying the particles.

Figure 8A:
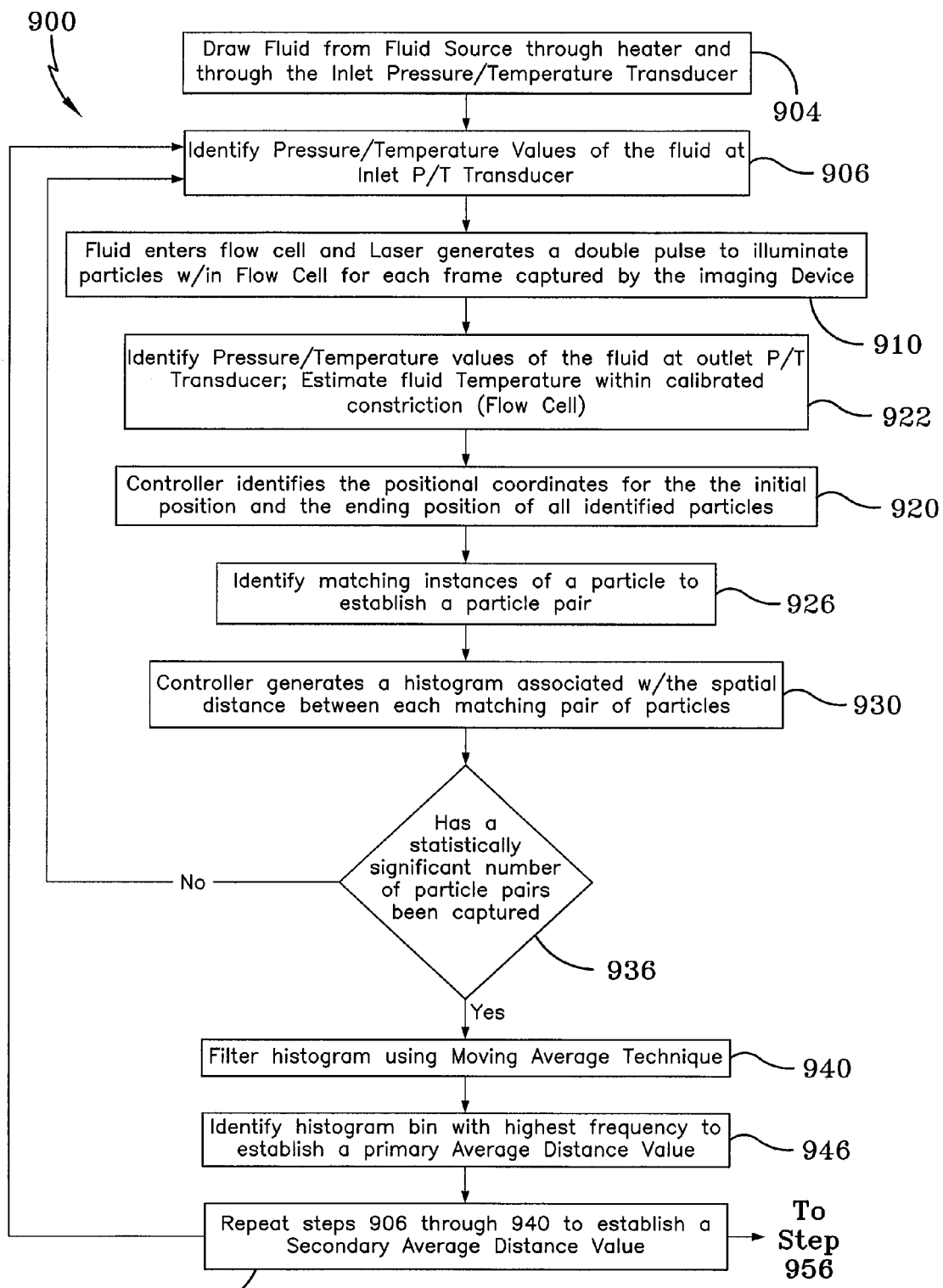
FIGS. 8A-B is a flow diagram showing the operational steps taken by the viscometer system to determine the viscosity of a fluid in accordance with the concepts of the present invention.
Figure 8B:
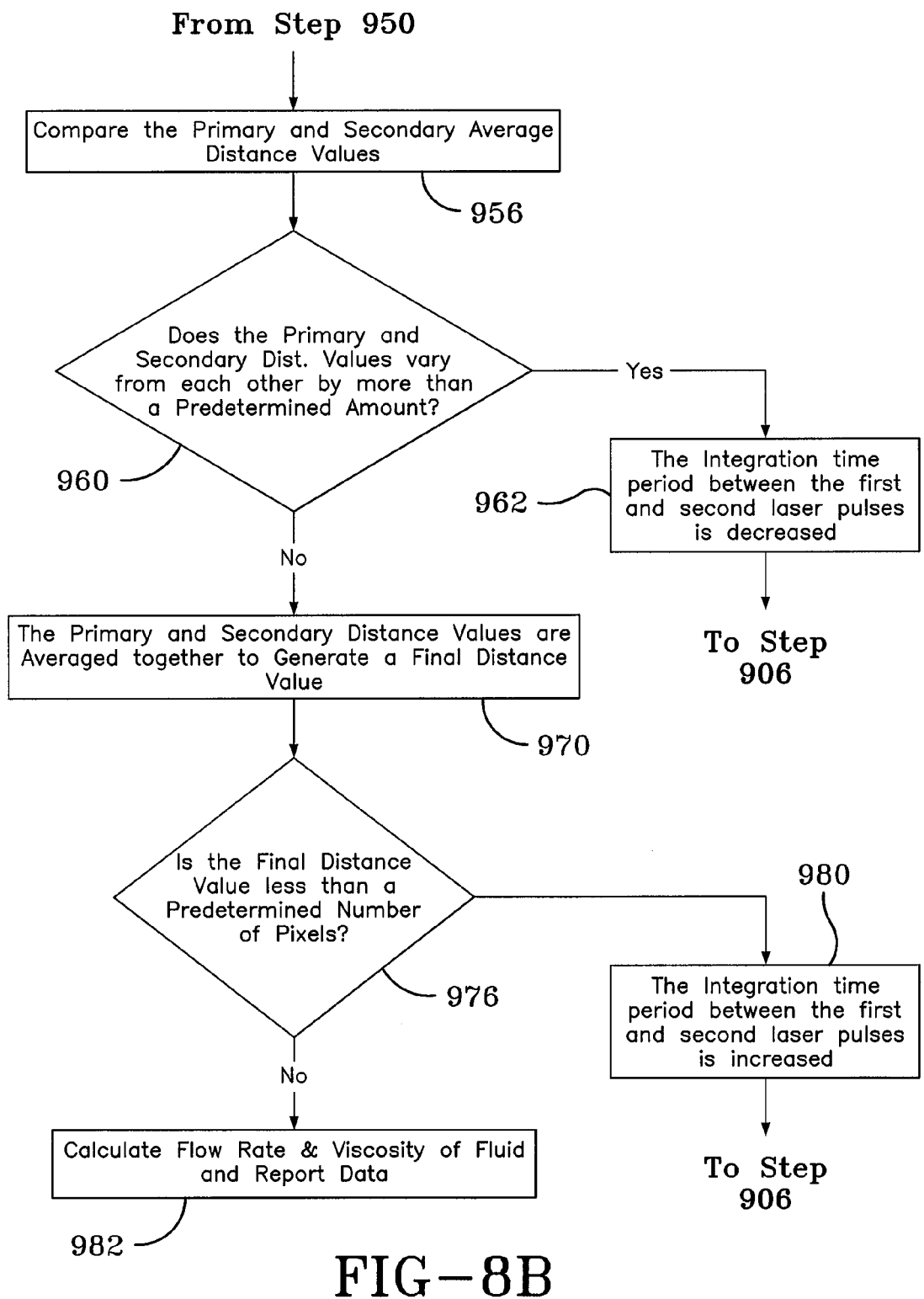

With the structural aspects of the system 10 set forth, the following discussion will now present the operational steps, generally referred to by the numeral 900, as shown in FIG. 8, for determining the viscosity of fluid being analyzed by the system 10.

Figure 9:
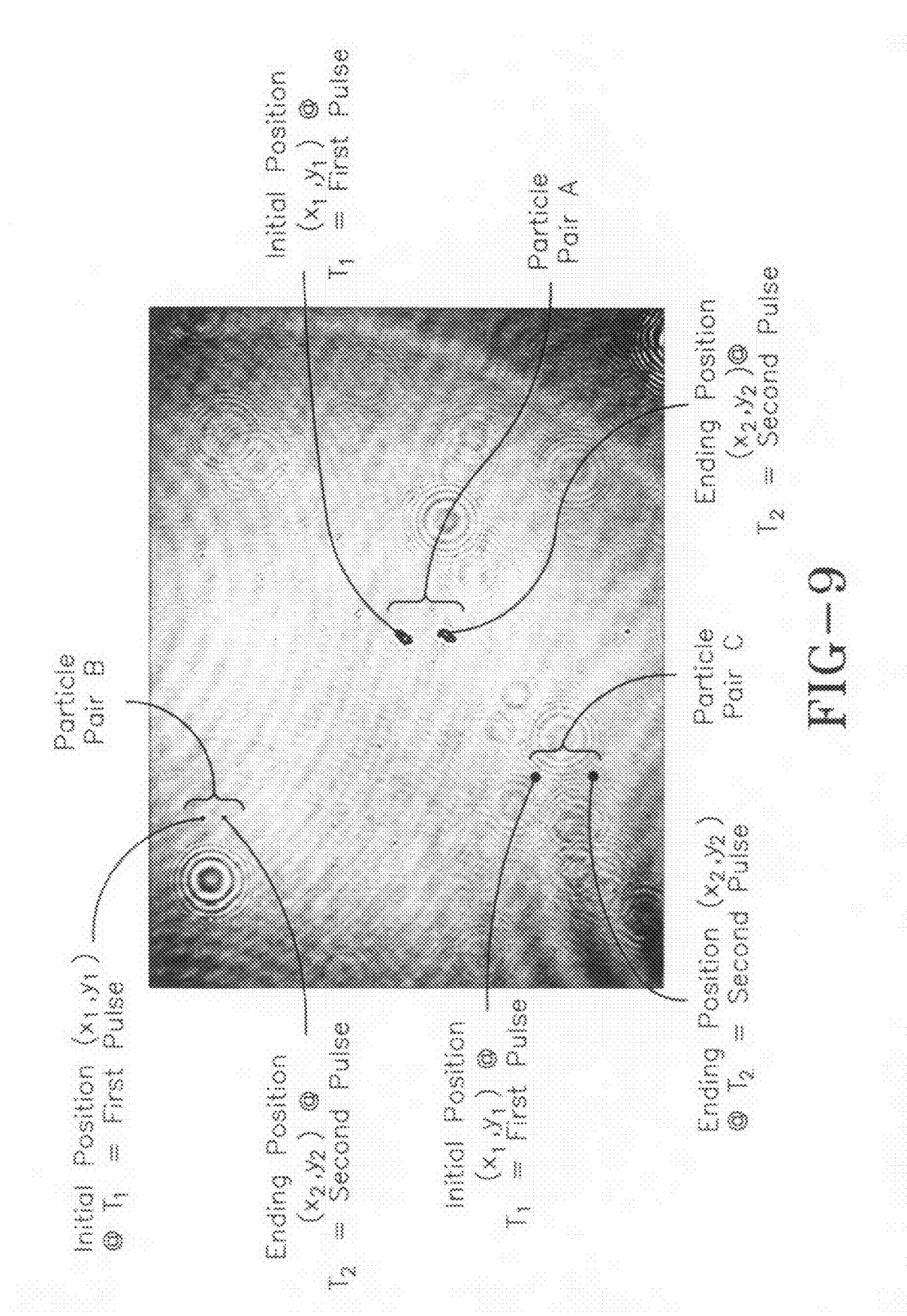
FIG. 9 is an annotated photograph showing the movement of particles imaged by the viscometer system in accordance with the concepts of the present invention.

Initially, at step 904, fluid is drawn from the fluid source 90 and into the heater 70 by operation of the pump 80, or other pressure differential, where the fluid is heated to any desired temperature, such as 40 or 100 degrees Celsius for example. It should also be appreciated that the pump 80 is configured or otherwise controlled to pump the fluid at a rate of approximately 2 mL/minute, although other rates may be used. After the fluid is optionally heated to the desired temperature, it flows through the inlet pressure/temperature transducer 200, where the pressure and temperature of the fluid is determined by the pressure sensing element 800 and the temperature sensing element 670, and stored at the controller 100, as indicated at step 906. Once the fluid exits the pressure/temperature transducer 200, the process continues to step 910 whereupon the fluid enters the flow cell 20 where various particles carried by the fluid are identified by the imaging system 160. As shown in FIG. 9, the light source 170, such as a laser, is pulsed twice during each frame of video that is integrated by the imaging device 180. As such, the separation time period is defined by as the elapsed time between the first pulse ($T_1$) of the laser, and the second pulse ($T_2$) of the laser. Furthermore, the elapsed time established by the separation time period between the first ($T_1$) and second ($T_2$) pulses of the laser 170 identifies the total time for which an identified particle has traveled during each imaged frame. For example, the time period between the first ($T_1$) and second ($T_2$) light pulses may be approximately 600 microseconds, although any other suitable time period may be used. It should also be appreciated that the due to the operation of the imaging device 180, imaged particles are digitally represented by the controller 100 as pixel locations, or a group of pixel locations that are identified by the two-dimensional positional coordinates X (column) and Y (row). Furthermore, the size of the imaging device 180 may be selected to provide different degrees of resolution, or to provide a larger imaging area in which particles can be imaged. Thus, after the particles have been integrated or imaged by the imaging device 180, the process continues to step 920, where the controller 100 identifies the positional coordinates (X,Y) of all particles identified in the imaged video frame. For example, as shown in FIG. 9, the controller 100 identifies pixels associated with the initial position ($X_1,Y_1$) of a particle imaged during the first pulse ($T_1$), and identifies pixels associated with the ending position ($X_2,Y_2$) of a particle imaged during the second pulse ($T_2$) of the video frame.

Somewhat simultaneously with step 920, step 922 is performed whereby the controller 100 determines and stores the temperature and pressure of the fluid as it exits the flow cell 20 via the outlet pressure/temperature transducer 210. In particular, the controller 100 processes, or otherwise averages the fluid temperature values identified at the inlet and outlet tubes 30,40 to estimate, or predict, the temperature of the fluid passing through the calibrated constriction maintained by flow cell 20. This estimated temperature is then associated with particular viscosity values derived using the process 900.

Continuing to step 926, once the initial position ($X_1, Y_1$) and ending positions ($X_2,Y_2$) of the imaged particles are identified, the controller 100 initiates the identification of particle pairs that appear in the imaged frame. Such a process is required as particles identified in the initial position ($X_1, Y_1$) may not be imaged by the imaging device 180 so as to have an ending position ($X_2,Y_2$) and vice versa. For the purposes of the following discussion, the term "particle pair" refers to a single particle that is associated with both an initial position ($X_1,Y_1$) and an ending position ($X_2,Y_2$). As such, the controller 100 undertakes to identify which initial position ($X_1, Y_1$) and ending position ($X_2,Y_2$) are associated with an individual particle, so as to form a particle pair, such as those particle pairs referred to by the identifiers A-C, as shown in FIG. 9, for example. Thus, to identify particle pairs, the controller 100 analyzes the positional coordinates of both the initial position ($X_1, Y_1$) and ending position ($X_2,Y_2$) of all of the particles imaged in the video frame. Specifically, the controller 100 may identify the initial position ($X_1, Y_1$) of a particular particle, and then analyze the region about the initial position ($X_1, Y_1$) in an effort to identify a particle that is in an ending position ($X_2,Y_2$), which is likely to have moved from the initial position ($X_1, Y_1$). For example, the controller 100 may identify particle pairs by analyzing a region of about the initial position ($X_1, Y_1$) of an imaged particle, and then gradually analyzing a region that diverges therefrom in the direction of the flow of the fluid. Alternatively, the controller 100 may assess the physical characteristics of the particles themselves so as to match the particle associated with the initial position ($X_1, Y_1$) with the particle image identified at the ending position ($X_2,Y_2$) to determine if the particle images match each other. That is, the controller 100 may analyze the shape, density, or other physical characteristics of the imaged particles to identify which particle images share the same characteristics, so as to determine which particle is associated with an initial position ($X_1, Y_1$) and ending position ($X_2,Y_2$).

Next, once the particle pairs for a given frame have been identified, the process continues to step 930, where the controller 100 generates a histogram based on the spatial distance, quantified in pixels, between the initial position ($X_1, Y_1$) and the ending position ($X_2,Y_2$) of the identified particle pairs. In particular, the histogram comprises a plurality of bins that are defined by the total number of imaging pixels maintained by the imaging device 180. In one aspect, the number of bins maintained by the histogram is determined by the resolution of the imaging device 180 and the manner in which the imaging device 180 is oriented with respect to the direction of flow of the fluid through the flow cell 20. That is, if the imaging device 180 has a resolution of 640×480 pixels, the imaging device 180 may be oriented such that the direction of flow through the flow cell 20 is aligned with the 640 pixel dimension, such that any particles must traverse this dimension before exiting the flow cell 20. As such, the number of bins used by the histogram is made equal to the 640 pixel dimension of the imaging device 480, such that 640 bins are provided in 1 pixel increments.

For each instance where a particle pair has been identified, the separation distance between the initial position ($X_1, Y_1$) and the ending position ($X_2,Y_2$) is calculated and applied to the bin that corresponds to the calculated separation distance value. For example, bin 1 would contain the aggregate number of separation distances that are equal to 1 pixel, while bin 300 would contain the aggregate number of separation distances that are equal to 300 pixels, and so on. Once the histogram has been updated with the particle separation distances of the identified particle pairs of a given imaging frame, the process continues to step 936, where the controller 100 determines whether a statistically significant number of particle pairs has been identified. If a statistically significant number of particle pairs have not been identified, then the process repeats steps 906-930, whereby additional video frames are imaged until a sufficient number of particle pairs have been identified. For example, the steps 906-930 may be repeated until approximately 300-400 video frames have been captured, so as to yield the identification of a statistically significant number of particle pairs. However, it should be appreciated that any suitable number of video frames may be imaged, so as to yield the identification of a statistically significant number of particle pairs.

Once a statistically significant number of particle pairs have been identified at step 936, then the process continues to step 940, where the controller 100 filters the histogram using a moving average process. In particular, the moving average technique serves to reduce any error that may result in determining the separation distance between the initial position ($X_1, Y_1$) and the ending position ($X_2,Y_2$) established by an identified particle pair. The moving average technique involves summing the aggregate number of frequency values within all the bins maintained within a moving window of a predetermined size, and then dividing the amount by the size of the moving window. For example, the 640 bins of the histogram are filtered by the moving average technique using a moving window having a size of 15 bins for example, although moving windows of other suitable sizes may be used. After the moving average of the histogram is performed, a resultant averaged histogram is generated, whereby the histogram with the highest magnitude is identified as the primary average distance value, as indicated at step 946. In other words, the bin with the highest magnitude represents the average distance traveled by the particles imaged by the system 10. Once the primary average distance value has been identified, the process continues to step 950 where the controller 100 repeats steps 906-946 so as to generate a second average distance value, which is compared to the primary particle distance value, as indicated at step 956. Somewhat simultaneously with step 956, step 960 is performed, whereby the process determines if the primary and secondary average distance values differ from one another by more than a predetermined amount. If the primary and secondary average distance values differ from one another by more than a predetermined amount, then the process continues to step 962, whereby the controller 100 decreases the separation time period (time delay) between the first ($T_1$) and second ($T_2$) laser pulses generated by the light source 170. And upon completion of step 962 the process returns to step 906. However, if at step 960, the primary and secondary average distance values do not vary from each other by more than a predetermined amount the process continues to step 970.

At step 970 then the primary and secondary average distance values are averaged together to generate a final distance value (D). Next, at step 976 the process 900 determines whether the final distance value is less than a predetermined number of pixels, such that if the final distance value is less than a predetermined number of pixels, the process continues to step 980. At step 980, the controller 100 increases the separation time period (time delay) between the first ($T_1$) and second ($T_2$) laser pulses in an attempt to generate more identifiable particle pairs, whereupon the process returns to step 906. However, if the controller 100 determines that the final average distance value identified in step 976 is not less than a predetermined number of pixels, then the process continues to step 982, where the controller 100 determines the flow rate of the fluid through the flow cell 20 using the formula:

$$\text{Flow Rate} = \frac{\text{Final Average Distance Value}(D)}{\text{Integration Time Period}(T2 - T1)}.$$

After the flow rate of the fluid has been calculated, the controller 100 ascertains the change in the pressure of the fluid identified by the first and second transducers 200,210 and stored at the controller 100. The controller 100 then calculates the viscosity of the fluid at a measured temperature by using the formula:

$$\text{Viscosity}(measured temperature) = K \cdot \frac{\text{Pressure Change}}{\text{Flow Rate}},$$

where K is the constriction constant value that defines the resistance to the flow of fluid through the flow cell 20. And at step 982, the controller displays the calculated information related to flow rate, viscosity, K and any data collected or observed by the system 10 in determination thereof. In addition, the estimated temperature of the fluid within the calibration constriction of the flow cell 20 identified at step 922 is also associated with the derived viscosity value calculated at step 982. As such, the system 10 provides fluid viscosity data at a given temperature, which is generally required when viscosity information is subsequently analyzed, extrapolated or reported. The display or output of this information and data may be shown on the display 306 or provided in a computer-readable format that is accessible and displayed in any number of ways available to those skilled in the art via the input/output device 304.

While the temperature change of the fluid as it moves from the inlet tube 30 to the outlet tube 40 may be identified, it is not necessary for the calculation of viscosity, and thus the temperature sensing element 670 may be omitted from the viscometer system 10. However, the ability to identify the viscosity of a fluid at a given temperature is highly desirable, and as such, is permitted by the system 10 to be identified and associated with a given viscosity value.

It should also be appreciated that the constriction constant value K that defines the resistance to the flow of fluid through the flow cell 20 may be determined by analyzing a fluid having a known viscosity at a given temperature. As such, the flow rate of the fluid can be determined using the equation:

$$\text{Flow Rate} = \frac{\text{Final Average Distance Value}(D)}{\text{Integration Time Period}(T2 - T1)},$$

and the process set forth above. While the constriction constant value K can be determined using the equation:

$$K = \text{Viscosity}(measured temperature) \cdot \frac{\text{Flow Rate}}{\text{Pressure Change}}.$$

Determining the constriction constant value K after the installation of the system 10 ensures that the various physical characteristics of the system 10 that can potentially influence the calculation of the constant value K are considered. For instance, variations in positioning of the pressure/temperature transducers 200,210 relative to the flow cell 20, and other physical characteristics unique to the particular installation are accounted for when computing the constant value K.

It will, therefore, be appreciated that one advantage of one or more embodiments of the present invention is that a viscometer provides a pressure/temperature transducer that can be added-on to an existing flow cell to enable the determination of the viscosity of a fluid passing therethrough. Another advantage of the present invention is that the viscometer is able to ascertain the viscosities of a fluid over a wide range of fluid types. Still yet, an additional advantage of the present invention is that the viscometer is able to determine the viscosity of a fluid over a wide range of temperatures. An additional advantage of the present invention is that the viscometer enables the determination of the viscosity of a fluid at a reduced cost as compared to other systems. Furthermore, another advantage of the present invention is that the viscometer enables the determination of the viscosity of a fluid having low or extremely low flow rates.

Although the present invention has been described in considerable detail with reference to certain embodiments, other embodiments are possible. Therefore, the spirit and scope of the appended claims should not be limited to the description of the embodiments contained herein.

What is claimed is:

1. A system for determining the viscosity of a fluid, the system comprising:
   a flow cell having an inlet and an outlet, and a calibrated constriction defined by a constant value K;
   an imaging system coupled to said flow cell to identify particles flowing therethrough;
   a first pressure transducer fluidly coupled to the inlet of said flow cell inlet, said inlet pressure transducer receiving a flow of fluid;
   a second pressure transducer fluidly coupled to said flow outlet; and a controller adapted to be coupled to said first and second pressure transducers, and to said imaging system, wherein said controller is configured to receive and compare particle images from the imaging system to determine a distance moved by each imaged particle during a predetermined period of time and determine a flow rate of the fluid based on an average of distance values and said predetermined period of time, and wherein said controller determines the viscosity of the fluid based on the constant value K associated with the flow cell, said flow rate and said change in pressure in the fluid at said first and second pressure transducers.

2. The system of claim 1, further comprising:
a bypass valve fluidly coupled between said first and second pressure transducers, such that when said bypass valve is in a first position, fluid flows through said flow cell, and when in a second position, fluid flows through said bypass valve thereby bypassing said flow cell.

3. The system of claim 1, further comprising:
a first temperature sensor fluidly coupled to said flow cell inlet; and
a second temperature sensor fluidly coupled to said flow cell outlet, wherein said temperature sensors are coupled to said controller, and wherein said controller determines the temperature of the fluid within said calibrated constriction based on temperature values identified by said first and second temperature sensors.

4. The system of claim 3, further comprising:
a heater coupled to said controller and fluidly coupled to said inlet pressure transducer to heat the fluid to a desired temperature.

5. The system of claim 3, wherein said first pressure transducer and said first temperature sensor are maintained by an inlet manifold and said second pressure transducer and said second temperature sensor are maintained by an outlet manifold.

6. The system of claim 5, wherein said inlet manifold comprises:
a body maintaining an inlet port and an outlet port that each extends into a flow basin, wherein said inlet port and said outlet port are laterally offset from each other; and
a seal disposed about a perimeter of said flow basin, wherein said first pressure transducer is disposed thereon, such that fluid flows through said flow basin and in contact with said pressure transducer.

7. The manifold of claim 6, wherein said flow basin comprises an annular base surface that is bounded by a wall surface that extends therefrom.

8. The manifold of claim 7, wherein said inlet port and said outlet port extend through said base and said wall surface.

9. The manifold of claim 6, further comprising:
an attachment bore that is fluidly coupled to said inlet port, said attachment bore configured to maintain said first temperature transducer.

10. The system of claim 5, wherein said outlet manifold comprises:
a body maintaining an inlet port and an outlet port that each extends into a flow basin, wherein said inlet port and said outlet port are laterally offset from each other; and
a seal disposed about a perimeter of said flow basin, wherein said second pressure transducer is disposed thereon, such that fluid flows through said flow basin and in contact with said pressure transducer.

11. The manifold of claim 10, wherein said flow basin comprises an annular base surface that is bounded by a wall surface that extends therefrom.

12. The manifold of claim 11, wherein said inlet port and said outlet port of said outlet manifold extends through said base and said wall surface.

13. The manifold of claim 10, further comprising:
an attachment bore that is fluidly coupled to said inlet port, said bore configured to maintain said second temperature transducer.

14. A method for determining a viscosity of a fluid flowing through a flow cell comprising:
providing a flow cell with a constriction having a flow resistance defined by a predetermined constant value, said flow cell having an inlet and an outlet, said flow cell configured to receive a flow of fluid therethrough;
providing an imaging system associated with said flow cell to image and detect the movement of at least one particle in the fluid;
coupling a first pressure transducer at said inlet and a second pressure transducer at said outlet;
determining a flow rate of the fluid through said flow cell based on a change in position of at least one imaged and detected particle in a predetermined period of time;
determining a change in pressure of the fluid between said inlet and said outlet of said flow cell; and
calculating a viscosity of the fluid based on said flow rate, said change in fluid pressure, and said predetermined constant value.

15. The method of claim 14, further comprising:
coupling a first temperature sensor at said inlet and a second temperature sensor at said outlet;
determining the temperature of the fluid within said constriction based on the temperature values identified by said first and second temperature sensors; and
reporting the temperature of the fluid within said calibrated constriction associated with said viscosity identified at said calculating step.

16. The method of claim 14, further comprising:
maintaining said first and second pressure transducers within respective manifolds having an inlet port and an outlet port, said inlet and outlet ports fluidly coupled to a flow basin, such that said inlet and outlet ports are laterally offset from one another.

17. The method of claim 16, further comprising:
providing said flow basin with a substantially annular base surface from which extends a wall.

18. The method of claim 17, further comprising:
extending said inlet and said outlet ports of said first and second pressure transducers through said base surface and said wall.

19. A manifold for determining a pressure of a flow of fluid via a pressure sensing element, said manifold comprising:
a body maintaining an inlet port and an outlet port that each extend into a flow basin, wherein said inlet port and said outlet port are laterally offset from each other; and
a seal disposed about the perimeter of said flow basin, wherein the pressure sensing element is disposed thereon, such that fluid flows between the inlet port and the outlet port and in contact with the pressure sensing element.

20. The manifold of claim 19, wherein said flow basin comprises an annular base surface that is bounded by a wall surface that extends therefrom.

21. The manifold of claim 20, wherein said inlet port and said outlet port extend through said base and said wall surface.

22. The manifold of claim 21 further comprising:
an attachment bore that is fluidly coupled to said inlet port, said attachment bore adapted to receive a temperature sensing element to detect the temperature of the fluid.

23. A method of determining the viscosity of a fluid flowing through a flow cell at a desired temperature comprising:
providing a flow cell maintaining a constriction, the flow through which is defined by a constant value K, and an imaging system configured to generate a light pulse to image particles carried by the fluid passing through the flow cell;
providing a pressure transducer to monitor a change in pressure of the fluid flowing through the flow cell;
determining a distance moved by each imaged particle during a predetermined period of time; and
identifying a flow rate of the fluid based on the average of the distance values and said predetermined period of time; and
determining a viscosity of the fluid based on said constant value K, the flow rate of the fluid, and the change in pressure of the fluid as it passes through the flow cell at the desired temperature.

24. The method of claim 23, wherein said first determining step comprises:
generating a first light pulse to establish an initial position of at least one imaged particle;
generating a second light pulse a predetermined time after said first generating step to establish an ending position of the at least one imaged particle;
associating the initial position and the ending position with a specific particle;
determining the distance between the initial position and the ending position for each specific particle identified at said associating step; and
averaging the distance values identified at said third determining step to identify an average distance value.

* * * * *